(12) United States Patent
Mullen

(10) Patent No.: US 7,148,031 B2
(45) Date of Patent: Dec. 12, 2006

(54) SEQUESTERING OF GLYCOPROTEIN MOLECULES AND OLIGOSACCHARIDE MOIETIES IN LIPO-GLYCOPROTEIN MEMBRANES AND MICELLES

(75) Inventor: Elaine Mullen, Alexandria, VA (US)

(73) Assignee: The Mitre Corporation, McLean, VA (US)

( * ) Notice: Subject to any disclaimer, the term of this patent is extended or adjusted under 35 U.S.C. 154(b) by 589 days.

(21) Appl. No.: 10/268,945

(22) Filed: Oct. 11, 2002

(65) Prior Publication Data

US 2003/0032770 A1 Feb. 13, 2003

Related U.S. Application Data

(63) Continuation-in-part of application No. 09/372,644, filed on Aug. 12, 1999, now Pat. No. 6,528,092, which is a continuation-in-part of application No. 08/280,520, filed on Jul. 26, 1994, now abandoned.

(51) Int. Cl.
*C12Q 1/34* (2006.01)

(52) U.S. Cl. ...................................................... 435/18

(58) Field of Classification Search .................. None
See application file for complete search history.

(56) References Cited

U.S. PATENT DOCUMENTS

| | | | |
|---|---|---|---|
| 2,583,096 A * | 1/1952 | Hadidian et al. ........... | 435/272 |
| 4,409,248 A | 10/1983 | Lenhardt et al. | |
| 4,725,442 A | 2/1988 | Haynes | |
| 4,790,987 A | 12/1988 | Compans et al. | |
| 5,071,964 A | 12/1991 | Dustin et al. | |
| 5,084,289 A | 1/1992 | Shin et al. | |
| 5,141,751 A | 8/1992 | Tomikawa et al. | |
| 5,188,837 A | 2/1993 | Domb | |
| 5,292,499 A | 3/1994 | Evans et al. | |
| 5,366,958 A | 11/1994 | Weiner et al. | |
| 5,824,337 A | 10/1998 | Mullen | |
| 6,528,092 B1 | 3/2003 | Mullen | |

OTHER PUBLICATIONS

V.M. Paradkar & J.S. Dordick (1991). "Purification of glycoproteins by selective transport using concanavalin-mediated reverse micellar extraction," Biotechnology Progress vol. 7, pp. 330-334.*
K.G. Welinder (1976). "Covalent structure of the glycoprotein horseradish peroxidase (EC 1.11.1.7)," FEBS Letters vol. 72, pp. 19-23.*
E.F. Annison & W.T.J. Morgan (1952). "Studies in immunochemistry. 11. The isolation and properties of the human blood-group H substance," Biochemical Journal vol. 52, pp. 247-258.*
H. Tuppy & H. Schenkel-Brunner (1969). "Formation of blood-group A substance from H substance by an alpha-N-acetylgalactosaminyl transferase," European Journal of Biochemistry vol. 10, pp. 152-157.*
M. Rosenberg et al (1986). "Separation of amphipathic proteins based on adsorption to hexadecane:water interfaces," Preparative Biochemistry vol. 16, pp. 133-141.*
K.R. Anumula & P.B. Taylor (1991). "Rapid characterization of asparagine-linked oligosaccharides isolated from glycoproteins using a carbohydrate analyzer," European Journal of Biochemistry vol. 195, pp. 269-280.*
Awadé, A.C., and Efstathiou, T., "Comparison of three liquid chromatographic methods for egg-white protein analysis," *J. Chromatogr. B 723*:69-74, Elsevier (Feb. 1999).
Awadé, A.C., et al., "Two-step chromatographic procedure for the purification of hen egg white ovomucin, lysozyme, ovotransferrin and ovalbumin and characterization of purified proteins," *J. Chromatogr. A 677*:279-288, Elsevier (Aug. 1994).
Bernhisel-Broadbent, J., et al., "Allergenicity and antigenicity of chicken egg ovomucoid (*Gal d* III) compared with ovalbumin (*Gal d* I) in children with egg allergy and in mice," *J. Allergy Clin. Immunol. 93*:1047-1059, Elsevier (Jun. 1994).
Besler, M., and Mine, Y., "The Major Allergen from Hen's Egg White: Ovomucoid (*Gal d 1*)," *Internet Symposium on Food Allergens 1* :137-146 (Oct.-Dec. 1999) available at: http://www.food-allergens.de/symposium-vol. 1(4)/originals/besler-mine/besler-mine-frame.html.
Bogard Jr., W.C., et al., "A $Ser^{162}/Gly^{162}$ Polymorphism in Japanese Quail Ovomucoid," *J. Biol. Chem. 255*:6569-6574, American Society for Biochemistry and Molecular Biology (1980).
Dell, A., and Morris, H.R., "Glycoprotein Structure Determination by Mass Spectrometry," *Science 291*:2351-2356, American Association for the Advancement of Science (Mar. 2001).

(Continued)

*Primary Examiner*—Sandra Saucier
(74) *Attorney, Agent, or Firm*—Sterne, Kessler, Goldstein & Fox PLLC

(57) ABSTRACT

Spontaneous formation of a coherent membrane at the interface between a non-polar liquid and an aqueous solution of glycoprotein can be used to separate proteins and carbohydrates from tissue fluid and other complex mixtures. When volatile hydrocarbons are used to induce membrane formation, evaporation of organic and aqueous solvents leaves behind a delicate film or powder. The method for extracting glycoprotein from solution and sequestering it in floating membranes can be used to study environmental conditions or to remove carbohydrates from proteins in the tissues of living organisms. This technique can also be used for detecting proteins in solutions.

16 Claims, 4 Drawing Sheets

OTHER PUBLICATIONS

Flower, D.R., "The lipocalin protein family: structure and function," *Biochem. J. 318*: 1-14, Portland Press (Aug. 1996).

Gil, T., et al., "Theoretical analysis of protein organization in lipid membranes," *Biochim. Biophys. Acta 1376*:245-266, Elsevier (Nov. 1998).

Hoober, K.L., et al., "A Sulfhydryl Oxidase from Chicken Egg White," *J. Biol. Chem. 271*:30510-30516, American Society for Biochemistry and Molecular Biology (Nov. 1996).

Ibarrola, I., et al., "Identification of a polygalacturonase as a major allergen (Pla a 2) from *Platanus acerifolia* pollen," *J. Allergy Clin. Immunol. 113*:1185-1191, Elsevier (Jun. 2004).

Imanishi, Y., et al., "Retinosomes: new insights into intracellular managing of hydrophobic substances in lipid bodies," *J. Cell Biol. 166*:447-453, Rockefeller University Press (Aug. 2004).

Itoh, N., and Nagata, S., "A Novel Protein Domain Required for Apoptosis. Mutational Analysis of Human Fas Antigen," *J. Biol. Chem. 268*:10932-10937, American Society for Biochemistry and Molecular Biology (May 1993).

Kuberan, B., et al., "Preparation and isolation of neoglycoconjugates using biotin-streptavidin complexes," *Glycoconj. J. 16*:271-281, Kluwer Academic Publishers (Jun. 1999).

Laskowski Jr., M., et al., "Ovomucoid Third Domains from 100 Avian Species: Isolation, Sequences, and Hypervariability of Enzyme-Inhibitor Contact Residues," *Biochemistry 26*:202-221, American Chemical Society (1987).

Likhosherstov, L.M., et al., "Structures of the Carbohydrate Chains of the Riboflavin-Binding Glycoprotein from Hens'-Egg White IV Neutral Oligosaccharides of the Hybrid Type," *Soviet J. Bioorg. Chem.*, An English Translation of *Bioorganicheskaya Khimiya 17*:140-144 (English); 246-251 (Russian), Plenum Publishing Corp. (1991).

Matsuhashi, S., "Stimulation of Epidermal Growth by the Egg White and Yolk," *Japan. J. Exp. Med. 55*:45-51, Kinokuniya Company Ltd. (1985).

Matsushima, K., "An Undescribed Trypsin Inhibitor in Egg White," *Science 127*:1178-1179, American Association for the Advancement of Science (1958).

Messier, P., "Protein Chemistry of Albumen Photographs," *Topics in Photographic Preservation. 4*:124-135, Photographic Materials Group of the American Institute for Conservation of Historic and Artistic Works (1991) available at: http://albumen.stanford.edu/library/c20/messier1991a.html.

Nakane, S., et al., "Hen Egg Yolk and White Contain High Amounts of Lysophosphatidic Acids, Growth Factor-Like Lipids: Distinct Molecular Species Compositions," *Lipids 36*:413-419, American Oil Chemists Society (Apr. 2001).

Nardone, E., et al., "Biochemical characterization and crystal structure of a recombinant hen avidin and its acidic mutant expressed in *Escherichia coli,*" *Eur. J. Biochem. 256*:453-460, Blackwell Science Ltd. (Sep. 1998).

Natunen, J., et al., "Enzymatic synthesis of two lacto-*N*-neohexaose-related Lewis x heptasaccharides and their separation by chromatography on immobilized wheat germ agglutinin," *Glycobiology 4*:577-583, Oxford University Press (Oct. 1994).

Piskarev, V.E., et al., "Structures of the Carbohydrate Chains of the Riboflavin-Binding Glycoprotein of Hens'-Egg Protein. II. $^1$H NMR (500 MHz) Spectroscopy of the Main Neutral Oligosaccharides," *Soviet J. Bioorg. Chem.*, An English Translation of *Bioorganicheskaya Khimiya 15*:847-854 (English); 1546-1554 (Russian), Plenum Publishing Corp. (1989).

Piskarev, V.E., et al., "Structures of the Carbohydrate Chains of the Riboflavin-Binding Glycoprotein of Hens'-Egg Protein. III. $^1$H NMR Spectroscopy (500 MHz) of the Neutral Fucosylated Oligosaccharides," *Soviet J. Bioorg. Chem.*, An English Translation of *Bioorganicheskaya Khimiya 16*:544-548 (English); 951-959 (Russian), Plenum Publishing Corp. (1990).

Qin, H., et al., "Two-Dimensional Crystallization of Avidin on Biotinylated Lipid Monolayers," *Biophys. J. 68*:2493-2496, Rockefeller University Press (Jun. 1995).

Scott, P.G., and Dodd, C.M., "Self-Aggregation of Bovine Skin Proteodermatan Sulphate Promoted by Removal of the Three N-Linked Oligosaccharides," *Connect. Tissue Res. 24*:225-235, Gordon and Breach (1990).

Sheldon, P.S., and Bowles, D.J., "The glycoprotein precursor of concanavalin A is converted to an active lectin by deglycosylation," *EMBO J. 11*:1297-1301, Oxford University Press (1992).

Shoda, S., and Fujita, M., "Transglycosylation Mechanism of Endoglycanases from the Viewpoint of Oligosaccharide Synthesis," 5 pages (Jun. 15, 2001) available at: http://www.glycoforum.gr.jp/science/word/glycotechnology/GT-B01E.html.

Singer, S.J., and Nicolson, G.L., "The Fluid Mosaic Model of the Structure of Cell Membranes," *Science 175*:720-731, American Association for the Advancement of Science (1972).

Suzuki, T., et al., "Site-specific de-*N*-glycosylation of diglycosylated ovalbumin in hen oviduct by endogenous peptide: *N*-glycanase as a quality control system for newly synthesized proteins," *Proc. Natl. Acad. Sci. USA 94*:6244-6249, National Academy of Sciences (Jun. 1997).

Tertov, V.V., et al., "Human plasma *trans*-sialidase causes atherogenic modification of low density lipoprotein," *Atherosclerosis 159*:103-115, Elsevier (Nov. 2001).

Tikkanen, K., et al., "Purification of a Galactosyl-α1-4-galactose-binding Adhesin from the Gram-positive Meningitis-associated Bacterium *Streptococcus suis,*" *J. Biol. Chem. 270*:28874-28878, American Society for Biochemistry and Molecular Biology (Dec. 1995).

Trudel, J., and Asselin, A., "Detection of a glycosylated form of hen egg white lysozyme," *Biochem. Cell Biol. 73*:307-309, National Research Council of Canada (May-Jun. 1995).

Vučković, M., et al., "Inter-protein bonding and other molecular interactions in hen egg white," *J. Serb. Chem. Soc. 65*:157-166, Serbian Chemical Society, month unknown, 2000.

Wilson, I.B.H., et al., "Analysis of Asn-linked glycans from vegetable foodstuffs: widespread occurrence of Lewis a, core α1 ,3-linked fucose and xylose substitutions," *Glycobiology 11*:261-274, Oxford University Press (Apr. 2001).

Wong-Madden, S.T., and Landry, D., "Purification and characterization of novel glycosidases from the bacterial genus *Xanthomonas,*" *Glycobiology 5*:19-28, Oxford University Press (Feb. 1995).

Wu, X-R., et al., "*In vitro* binding of type 1-fimbriated *Escherichia coli* to uroplakins Ia and Ib: Relation to urinary tract infections," *Proc. Natl. Acad. Sci. USA 93*:9630-9635, National Academy of Sciences (Sep. 1996).

Yamamoto, K., et al., "Characterization of *Bacillus* sp. endo-β-*N*-acetylglucosaminidase and its application to deglycosylation of hen ovomucoid," *Biotechnol. Appl. Biochem. 28*:235-242, Portland Press (Dec. 1998).

Yamamoto, K., "Synthesis of Glycopeptide Using Endoglycosidase," 3 pages (Sep. 15, 2001) available at: http://www.glycoforum.gr.jp/science/word/glycotechnology/GT-B03E.html.

Dionex Corporation Technical Note 36, "Analysis of Exoglycosidase Digestions of *N*-Linked Oligosaccharides Using HPAE-PAD," pp. 1-12, Dionex Corp., Sunnyvale, CA, month unknown, 1995.

European Bioinformatics Institute, "Interpro: Glycoside hydrolase, family 1," 2 pages, available at: http://www.ebi.ac.uk/interpro/DisplayIproEntry?ac=IPR001360; created Oct. 1999, modified Nov. 2001.

* cited by examiner

MEMBRANE FORMATION

- 10 NON-POLAR LIQUID FLOATS ON SURFACE
- 11 MEMBRANE
- 12 AQUEOUS SOLUTION CONTAINING GLYCOPROTEIN

MEMBRANE VESICULATES WHEN AGITATED

21 VESICLES AND MICELLE-LIKE STRUCTURES

AGITATION

FORMATION OF DOUBLE MEMBRANE

GLYCOPROTEIN SOLUTION
INTRODUCED ABOVE MEMBRANE

MICROSCOPIC VIEW OF MEMBRANE DEVOID
OF SOLVENT

US 7,148,031 B2

SEQUESTERING OF GLYCOPROTEIN MOLECULES AND OLIGOSACCHARIDE MOIETIES IN LIPO-GLYCOPROTEIN MEMBRANES AND MICELLES

CROSS-REFERENCE TO RELATED APPLICATIONS

The present application is a continuation in part of Ser. No. 09/372,644, filed Aug. 12, 1999 now U.S. Pat. No. 6,528,092, which is a continuation in part of Ser. No. 08/280,520, filed Jul. 26, 1994 now abandoned, the entire contents of which are hereby incorporated by reference.

FIELD OF THE INVENTION

The present invention relates to protein separation wherein a glycoprotein is isolated from another material with which it was once associated. Because proteins isolated according to this invention are necessarily glycosylated, the invention also relates to carbohydrate separation.

BACKGROUND OF THE INVENTION

In living plant and animal cells, non-polar lipids are stored in droplets within the cytoplasm and are rarely found in biological membranes. Proteins which have been isolated from membranes of living cells often possess a sequence of non-polar amino acids which anchor the proteins through hydrophobic associations within the interior of phospholipid bilayers. Other proteins are anchored through covalent bonds to glycophospholipids. The oligosaccharide moieties of membrane glycoproteins and glycophospholipids project into the aqueous environment.

Phospholipid monolayers and bilayers form micelles and liposomes which have been used successfully in delivering pharmaceutical agents. However, the chemical and mechanical instability of these constructs have posed problems. Liposomes are prone to oxidation and tend to aggregate and fuse during prolonged storage. Injected liposomes are degraded by the lecithin-cholesterol acyl transferase of high density lipoproteins, and are cleared from the bloodstream by macrophages and hepatocytes. Though it is possible to attach certain glycoproteins to phospholipid micelles, polar phosphate heads facing the aqueous solution tend to inhibit contact of lipid tails with the hydrophobic amino acids of glycoproteins.

Both amino acid sequences and oligosaccharide segments of glycoproteins can contribute chemical and biological properties that may be useful in extracting proteins and glycoproteins from aqueous systems.

Sialic acid, the terminal sugar of may oligosaccharides produced in animal tissue, is ionized at pH 7 (Lehninger et al., 1993). Its presence inhibits uptake and degradation by hepatocytes in circulating blood cells and glycoproteins.

Micelles are aggregates of substances in which hydrophilic polar groups of compounds orient themselves toward and interact with the aqueous phase. The hydrophobic nonpolar hydrocarbon chains of the micelles are hidden within the structure. For example, micelles which contain soap molecules remain evenly suspended in water because their surfaces are negatively charged and the micelles repel each other. Micelles prepared from phospholipids and oligosaccharide-lipid complexes have been used to prepare vaccines using natural and synthetic oligosaccharides, which are immunogens, to prepare stabilized vaccines, as disclosed in U.S. Pat. No. 5,034,519, the entire contents of which are hereby incorporated by reference.

It is also known that amphipathic proteins such as cytochrome oxidase, an intrinsic enzyme found in mitochondrial membrane, when placed in suspension with lipids form sac-like vesicles that are, in effect, man-made membranes. These vesicles have been used as model systems for the study of the isolated protein's relationship with lipid bilayers.

Compans, in U.S. Pat. No. 4,790,987, teaches the preparation of viral glycoprotein subunit vaccines by complexing a lipid with the glycoprotein.

Compans also teaches that the complexes can be obtained by dissolving a lipid in a dialyzable detergent solution containing glycoproteins, then dialyzing the solution to obtain the protein-lipid complex. The lipids are phospholipids. The resulting complexes are then administered in pharmaceutically acceptable carriers.

Rutter et al., in U.S. Pat. No. 4,769,238, note that vaccine bound to a membrane may be superior to non-membrane bound proteins.

Mouritesen et al. have studied protein-protein and protein-lipid interactions in phospholipid bilayers in an attempt to refine the fluid mosaic model of biomembrane proposed in 1972 by Singer-Nicolson. In 1995 Oln et al. produced two-dimensional crystals of avidin on the hydrophobic surface of a phospholipid monolayer. In both synthetic and biological phospholipid membranes, polar heads of component molecules lie adjacent to one another at the aqueous interface, shielding their hydrophobic lipid tails from contact with water or molecules dissolved therein.

In U.S. Pat. No. 5,846,744, Athey et al. describe a novel sensor format based on the impedance analysis of polymer coatings on electrodes for determining the presence or amounts of an analyte in a sample of assay medium.

Organic solvents and detergents have long been used to separate proteins and carbohydrates from the tissues of plants and animals in which they were synthesized. However, deliberate removal from both solvents of a coherent film of glycoproteins fabricated at the oil-water interface is a novel method for separating glycoproteins and their oligosaccharide moieties from solution.

Current methods of glycoprotein recovery and separation often involve the addition of substances which interact chemically with the molecules to be extracted. For instance, dilution with water of soluble glycoproteins in hen egg white causes some components to denature and clump together. In order to facilitate the movement of proteins through gels, filters and other matrices used in the process of protein separation, oligosaccharide moieties are often intentionally removed.

Methods of producing lipo-glycoprotein membranes and micelles are disclosed in Mullen, U.S. Pat. No. 5,824,337, the entire contents of which are hereby incorporated by reference. Lipophilic amino acids of glycoproteins adhere through non-covalent hydrophobic interactions to molecules of oil, while hydrophilic moieties form hydrogen bonds with water molecules in the aqueous phase. In addition, proteins may adhere to one another in the plane of the oil-water interface through a variety of non-covalent associations, including sulfur bonds, to produce a membrane that is mechanically and chemically stable relative to a phospholipid membrane.

Carbohydrate moieties of glycoproteins are key components of various intercellular recognition processes. Glycoproteins on the outer surface of the micelle can be chosen to target appropriate tissue, inhibit uptake by tissue, and induce endocytosis of the micelle. Antibodies, apoproteins, and opsonins are examples of glycoproteins that mediate these responses.

SUMMARY OF THE INVENTION

It is an object of the present invention to overcome the aforesaid deficiencies in the prior art.

It is another object of the present invention to filter or sequester glycoproteins and their carbohydrate moieties using glycoprotein membranes so as to remove them from solution.

It is another object of the present invention to detect proteins, including antigens, in an aqueous medium using the formation or presence of glycoprotein membranes.

The present invention is based upon the discovery that many glycoproteins present in plant and animal tissue fluids spontaneously aggregate at the interface between aqueous solutions and non-polar liquids to form a flexible membrane. The phenomenon of lipo-glycoprotein membrane formation can be used to filter or sequester glycoproteins and their carbohydrate moieties for removal from solution. Through the process of lipo-glycoprotein membrane formation, trace concentrations of glycoprotein can be collected from aqueous media. Hydrated oligosaccharides that project into the aqueous solution can be chemically or enzymatically removed from floating membranes or subjected to study in situ.

Membranes and oil-filled vesicles can be separated from a suspending fluid, washed, and dried or introduced into a fresh aqueous medium such as water or saline solution. Microscopic micelles that remain in suspension can be recovered by a variety of methods, including centrifugation, filtration, evaporation, and electrokinetic migration.

In addition to its utility in the isolation of glycoproteins from complex solutions such as animal and plant tissue fluids, the separation method of the present invention can be used to sequester oligosaccharide moieties on the hydrophilic surfaces of micelles and lipo-glycoprotein membranes.

Washed glycans can be studied in situ or cleaved from proteins suspended in floating membranes and subsequently recovered from solution.

The synthetic membranes, micelles, and vesicles of the present invention form in response to the spontaneous orientation of hydrophobic and hydrophilic groups in aqueous media. Unlike phospholipid monolayers, micelles, and liposomes, the membranes of the present invention comprise a sheet of glycoprotein molecules associated on one face with a non-polar liquid, and on the other face with water. The oligosaccharide moieties of glycoprotein molecules are oriented toward the aqueous environment.

Lipo-glycoprotein membrane formation can be used to extract both glycoproteins and oils from aqueous solution. During the process of membrane formation, strong intermolecular attraction traps glycoproteins and hydrophobic liquids. Very small concentrations of glycoprotein and oil can be collected in membranes and removed mechanically from the surface of an aqueous solution. Volatile organic liquids are sequestered within micelles that form when the membrane is agitated.

Membrane formation can also be employed in sensor design. For example, an oil-filled tube having a small aperture can be inserted into an aqueous solution, then withdrawn and subjected to measurement of light absorption or penetration through the aperture to detect proteins therein. To sense the escape of solvents from an industrial process, a sample can be introduced into an aqueous solution of glycoprotein and agitated. The formation of micelles at the surface not only indicates the presence of hydrophobic chemicals, but also facilitates their recovery.

Hydrated glycans are preserved on membrane surfaces and can be studied in situ. The association of lipid with glycoproteins appears to maintain the orientation of carbohydrate moieties and facilitate the rehydration of dried micelles. oligosaccharide components prevent aggregation and fusion of micelles and inhibit their degradation by heat and protease.

Stable glycoprotein membranes of the present invention are prepared by first layering a non-polar liquid on top of an aqueous mixture containing at least one glycoprotein or proteoglycan. A membrane then forms at the aqueous-nonpolar interface plane. When agitated, the membrane breaks apart into vesicles and micelles having an oligosaccharide surface facing the aqueous solution and enclosing one or more hydrophobic substances. Gentle agitation of the membrane produces vesicles of sufficiently large diameter to permit easy removal from the aqueous solution in which they are dispersed. The large vesicles may then be passed through a strainer or screen to divide them into smaller micelles. Micelles produced by association of non-polar liquids with glycoproteins are mechanically and chemically more stable than those derived from phospholipids.

Additional details about membrane formation can be found in parent application Ser. No. 09/372,644, filed Aug. 12, 1999, the entire contents of which are hereby incorporated by reference.

DETAILED DESCRIPTION OF THE INVENTION

Hydrated molecules of glycoprotein dissolved in aqueous solution tend to associate in an orderly fashion at the interface with non-polar liquid hydrocarbons and lipids. Attraction of oil to hydrophobic amino acids, formation of hydrogen bonds between water molecules and polar groups of hydrophilic amino acids and oligosaccharide moieties, and non-covalent bonds between adjacent protein molecules act together to produce a coherent glycoprotein film at an oil-water interface. Floating lipo-glycoprotein membranes and oil-filled vesicles (micelles) can be removed from the aqueous solution in which they were fabricated. In a freshly prepared aqueous suspension, oil-filled lipo-glycoprotein micelles rise at a rate proportional to their respective diameters. Larger micelles contain a relatively greater amount of oil and rise more quickly to the top of the solution. At the surface, the largest vesicles are intercalated among smaller micelles. Laminar flow and attraction of micelles to container walls can cause errors in separation when tubes narrower than ¼ inch are used. The density differential produces a clear vertical separation of micelles greater than 10 microns in diameter. If a second aqueous solution is carefully added to the top of the first, larger micelles will rise through it, while microscopic micelles between 1 and 10 microns remain suspended in the original solution and may be extracted therefrom. Larger micelles containing materials which are more dense than oil will float in a layer containing smaller oil-filled micelles. Vertical separation can thus be used to distinguish micelles by the density of the contents thereof. Once a layer has been selectively extracted, the micelles can be separated by size exclusion.

Figure 1:
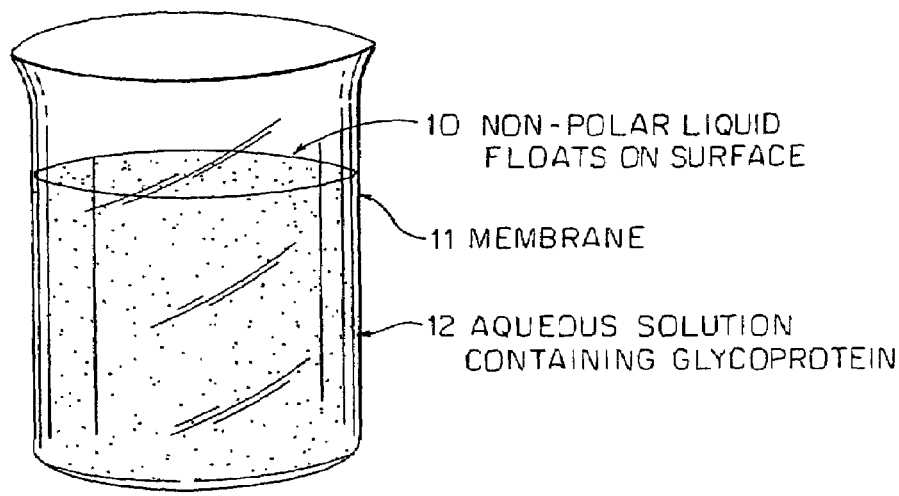
FIG. 1 illustrates membrane formation according to the present invention.
Figure 2:
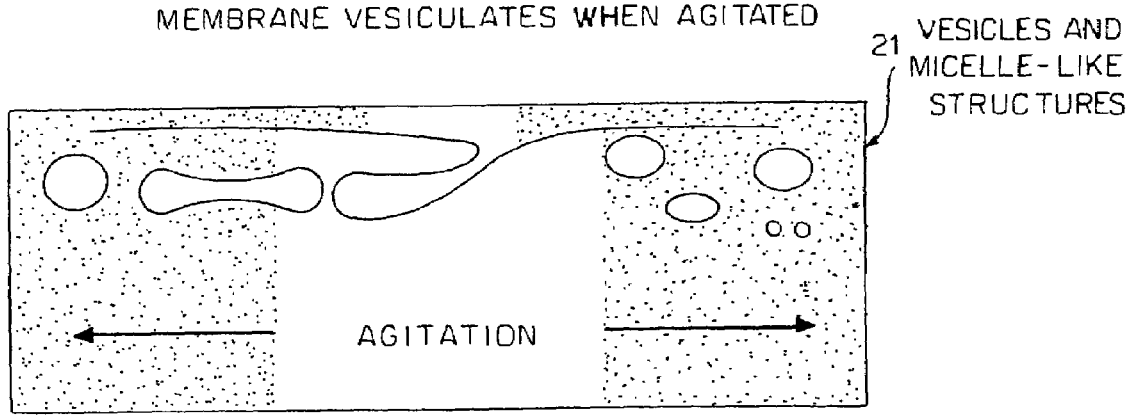
FIG. 2 shows how membrane breaks into vesicles and micelle-like structures.
Figure 3:
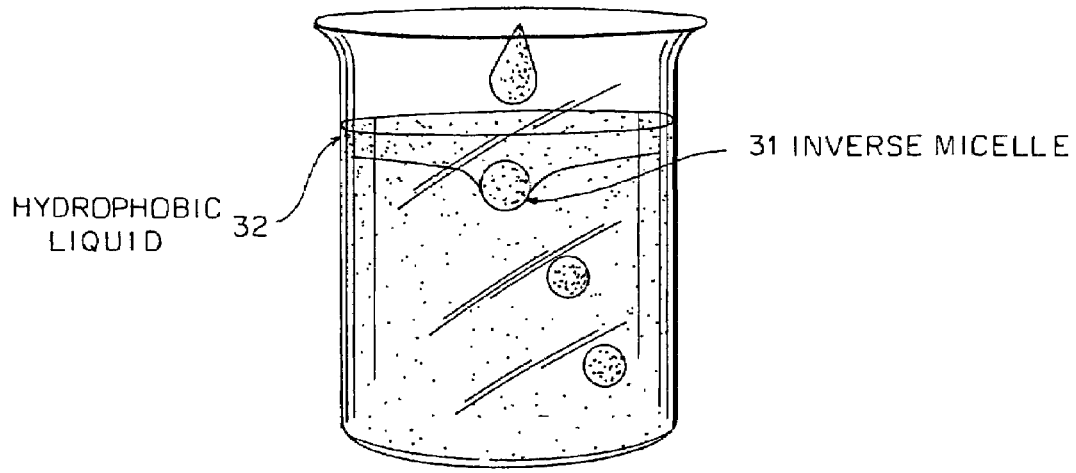
FIG. 3 shows formation of a double membrane.

Glycoproteins may be altered in vivo by physical and chemical processes. Care must be taken to obtain fresh samples that have not been subjected to enzymatic degradation or lysis. For example, glycoproteins from the whites of fertilized hen eggs or juices of bruised fruits often fail to form lipo-glycoprotein membranes.

Micelles made with egg white as the source of glycoprotein, when repeatedly passed through small pores, adhere to each other in aqueous solution. This phenomenon makes it possible to remove certain glycans mechanically during filtration.

Glycoproteins stored on the surfaces of oil-filled micelles can often be dried and then rehydrated. However, dried membranes lose their elasticity and are fragile. When volatile hydrocarbons are used to induce membrane formation, evaporation of organic and aqueous solvents leaves behind a diaphanous, brittle monolayer of glycoprotein. The structure of these delicate membranes can be studied using methods such as X-ray crystallography and electron microscopy to provide insight into protein-protein interactions.

Typically a powder or brittle film of glycoprotein remains on the substrate when water and organic solvents evaporate from the membrane or micelle. Extracted glycoprotein can often be dissolved in water. The process of micellar electrokinetic chromatography may also be used to separate glycoproteins and oligosaccharide moieties borne on surfaces of lipo-glycoprotein micelles.

Glycoproteins are isolated from solution by:

(1) layering a non-polar liquid on top of an aqueous mixture containing at least one glycoprotein or proteoglycan and (2) allowing a membrane to form at the interface between the aqueous and hydrophobic liquids.

The invention provides a method for extracting glycoprotein from a polar solution containing at least one glycoprotein comprising: (a) adding at least one non-polar liquid to a polar solution containing at least one glycoprotein; (b) whereby a layer of glycoprotein forms at an interface between said polar solution and said non-polar solution; and (c) replacing the solution described in step (a) with a second solution.

The invention further provides a method for extracting glycoprotein from a polar solution containing at least one glycoprotein comprising: (a) adding at least one non-polar liquid to the polar solution containing at least one glycoprotein; (b) whereby a layer of glycoprotein forms at an interface between said polar solution and said non-polar solution; (c) agitating the produce of step (b) until micelles form; and (d) collecting the micelles formed in step (c).

Also provided is a method for extracting glycoprotein from a polar solution containing at least one glycoprotein comprising: (a) adding at least one non-polar liquid to a polar solution containing at least one glycoprotein; (b) whereby a layer of glycoprotein forms at an interface between said polar solution and said non-polar solution; and (c) collecting the glycoprotein layer on a solid support or mesh.

The invention further provides a method for extracting carbohydrates from a polar solution containing at least one glycoprotein comprising: (a) adding at least one non-polar liquid to a polar solution containing at least one glycoprotein; (b) whereby a layer of glycoprotein forms at an interface between said polar solution and said non-polar solution; (c) replacing the solution described in step (a) with water; (d) treating the solution from step (c) with n-glycosidase to remove oligosaccharide moieties; and (e) separating liquid containing oligosaccharides from floating micelles containing protein and oil components.

Also provided is a method for detecting the presence of proteins in an aqueous solution comprising: (a) adding an oil to the aqueous solution to form a membrane with glycoproteins present in the solution; (b) withdrawing the membrane formed from the solution; (c) whereby the formation of a membrane indicates the presence of proteins in the aqueous solution. In embodiments, the oil is added through an oil-filled tube inserted into the aqueous solution, the tube is withdrawn, and light absorption of the tube is measured to detect proteins present therein.

The invention additionally provides, in a method for culturing a microorganism to obtain metabolites therefrom, the improvement comprising using a lipo-glycoprotein as a cultural medium. In embodiments, the microorganism is a mold or a bacteria.

FIG. 1 illustrates formation of membranes for making micelles according to the present invention. When a non-polar liquid 10 such as a lipid or saturated hydrocarbon is layered on the surface of an aqueous solution 12 containing glycoprotein, a membrane 11 forms at the interface. Additional substances can be added to the surface of the membrane.

When a lipo-glycoprotein membrane is rolled, shaken or forced through a filter, it stretches and breaks into closed micelles or vesicles. Large vesicles formed by gently agitating a membrane can often be lifted from solution on mesh with openings as large as 1.25 mm. Smaller micelles can be obtained by pouring the micelles through smaller mesh, by multiple passages through the mesh, or by increasing the pressure under which the liquid containing the micelles is forced through the mesh. Nylon filters having pores of 0.1 mm have been particularly useful for breaking large vesicles into smaller units ranging from about 1 to 5 microns in diameter. Pouring the mixture between two containers also produces smaller and smaller micelles as the process is repeated. Solutions containing large numbers of micelles having diameters between 2.5 microns and 1 micron have been obtained by using atomizers to produce a mist of glycoprotein into which oil is sprayed. Because metallic residues are absorbed by certain glycoproteins from stainless steel, nylon filters and glass or plastic containers are preferred for breaking up the membranes.

FIG. 2 shows that, when agitated, the membrane 11 of FIG. 1 breaks into large vesicles 21 and micelle-like structures 21.

A drop of aqueous solution containing glycoprotein, when introduced into a lipid floating above a glycoprotein membrane, will form a second membrane. This membrane-bound vesicle, with its hydrophobic face oriented toward the exterior, is essentially an “inverse” or “reverse” micelle. By virtue of its weight relative to oil, a large droplet will sink down, suspended by the original membrane, into the aqueous phase. With agitation, the droplet will stretch and break free of the surface membrane, completely enclosed within a double membrane. Sometimes a small oil-filled tube connects the outer glycoprotein envelope to the surface membrane from which it was derived.

FIG. 3 shows formation of a double membrane. Inverse micelles 31 can be added to or formed in the hydrophobic liquid 32 above the membrane. These micelles could include inverse phospholipid micelles which contain a hydrophilic drug. The compound vesicles so formed have a double membrane. The hydrophobic surfaces of the membranes eventually fuse, which makes these useful for delayed release of drugs.

Figure 4:
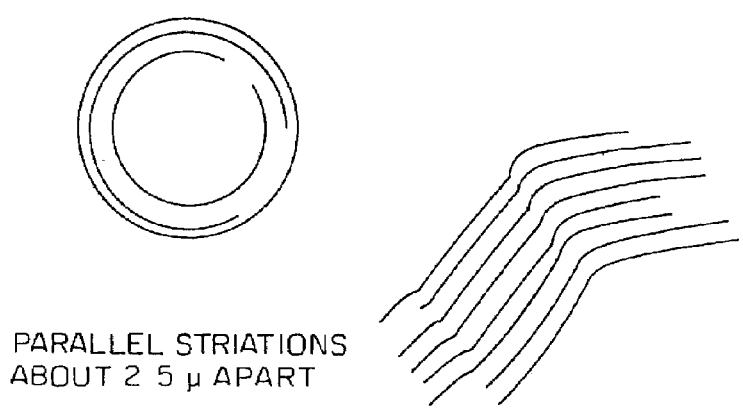
FIG. 4 illustrates the microscopic structure of a hexane-glycoprotein membrane.

When micelles are formed in a hydrocarbon liquid such as hexane or heptane, the micelles tend to stick together and occasionally float in the hexane layer. This indicates a different surface configuration from that of lipid-filled micelles, which float in the aqueous layer after formation. Heat or slight vacuum ruptures micelles containing hexane or heptane, leaving a fragile glycoprotein membrane on the substrate. Microscopic examination of a membrane formed from hexane and ovomucoid reveals parallel striations about 2.5 microns apart. This is illustrated in FIG. 4.

Figure 5:
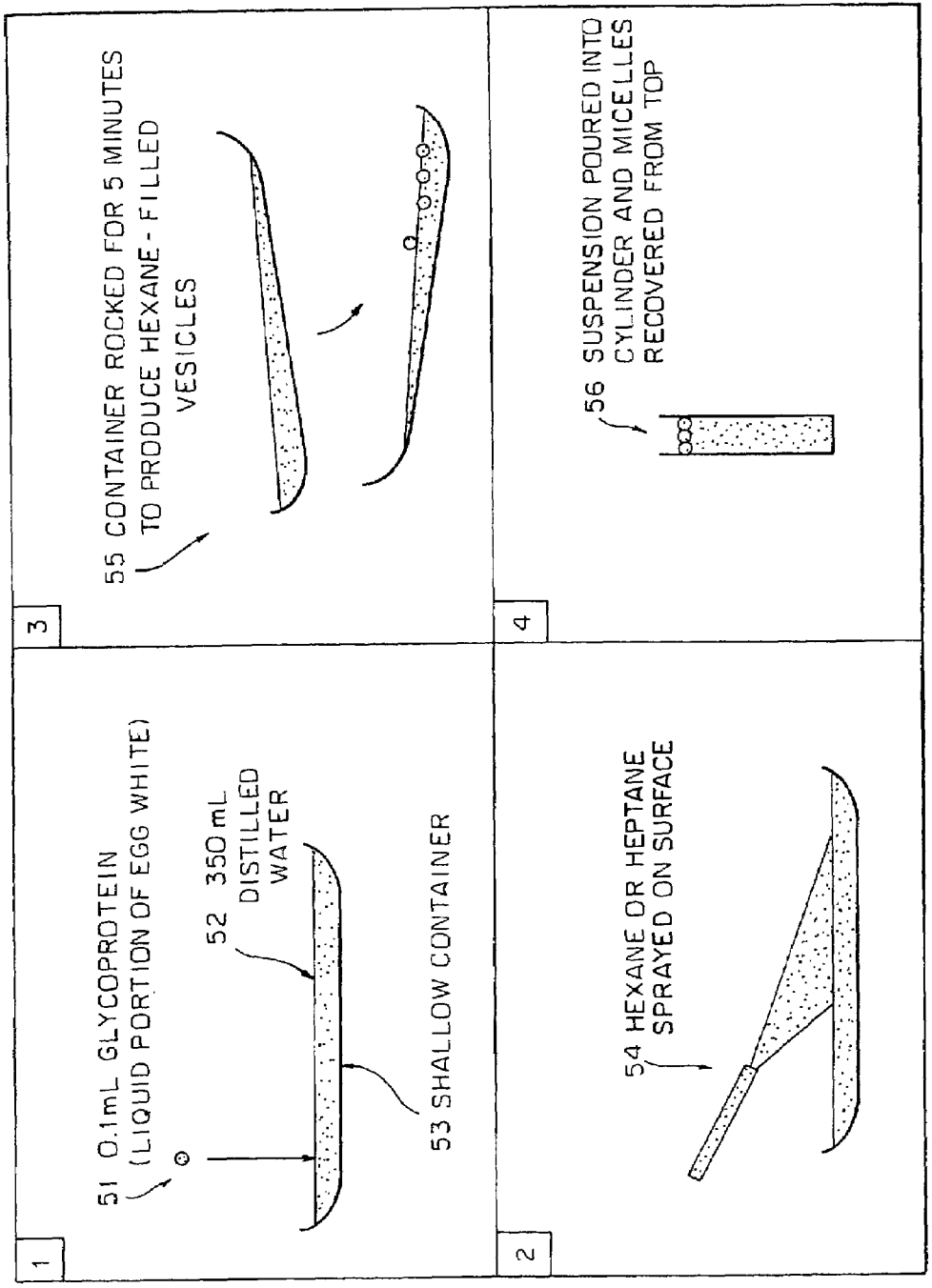
FIG. 5 shows how glycoprotein is recovered from water.

FIG. 5 shows recovery of glycoprotein from water. In the first frame, glycoprotein, from egg white, 51 is added to distilled water 52 in a container 53. Next, hexane or heptane or other non-polar liquid is sprayed onto the surface of the water 54. The container 55 is then rocked for about five minutes to produce hexane-filled vesicles. This suspension is poured into a cylinder 56. The micelles so formed 56 are recovered from the top of the cylinder.

Figure 6:
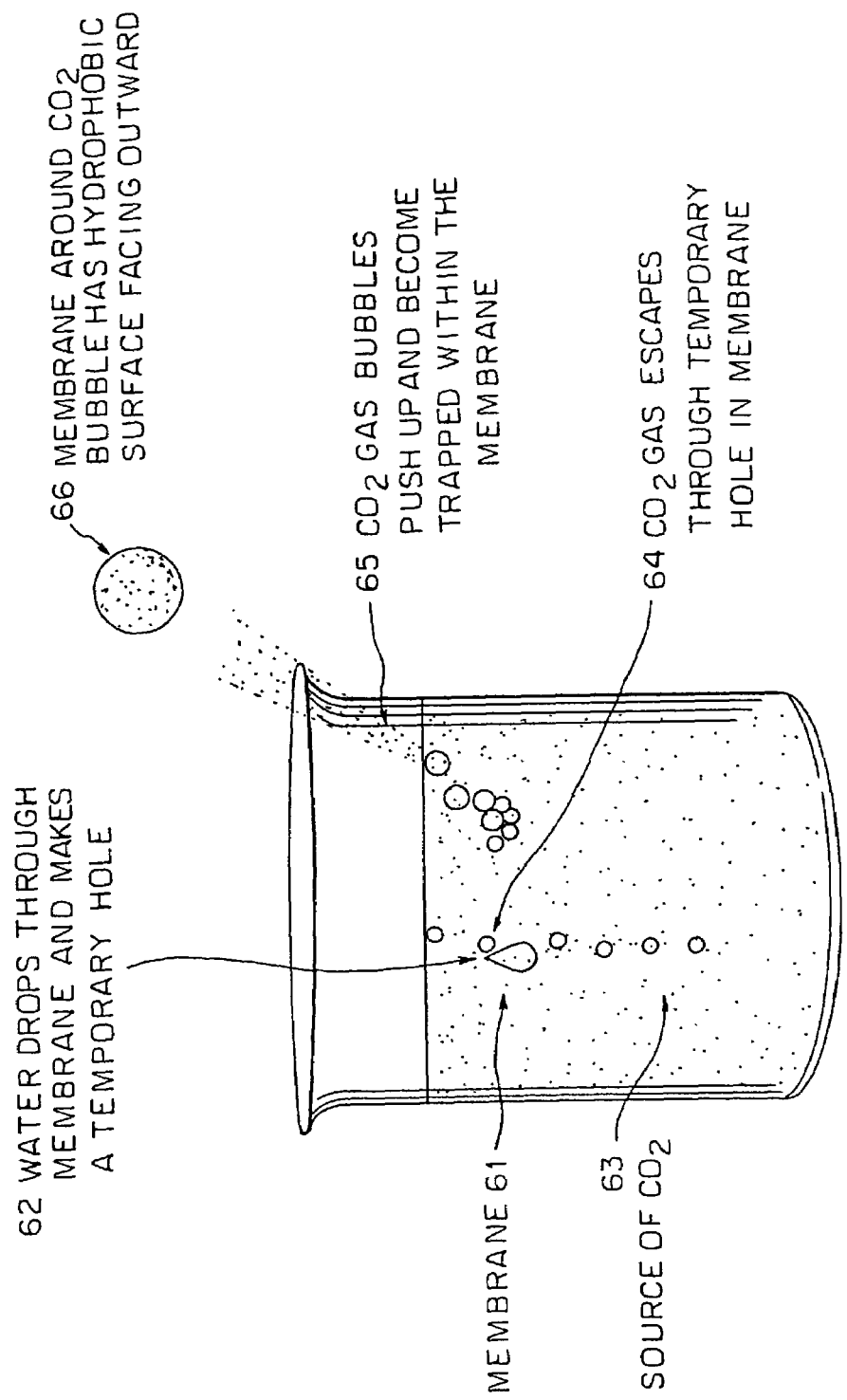
FIG. 6 illustrates trapping carbon dioxide.

As illustrated in FIG. 6, carbon dioxide can be trapped in the micelles of the present invention. First, a membrane 61 is formed on top of a source of $CO_2$ 63. Water is dropped through the membrane and makes a temporary hole 62 through which $CO_2$ gas 64 escapes. Carbon dioxide bubbles push up and become trapped within the membrane 65. The membrane around the $CO_2$ bubble 66 has its hydrophobic surface facing outward. When the bubble is punctured, the membrane persists, even after the $CO_2$ escapes.

The lipo-glycoprotein membranes are relatively stable chemically. The micelles do not break down when acids, bases, or surfactants are added to a liquid containing these micelles. However, alcohols can penetrate micellar membranes and change the properties of constituent molecules.

Organic solvents such as hydrocarbons, lipids, and liquid waxes can be trapped within a membrane and then mechanically separated from the surface of an aqueous solution. Membrane formation is induced by the addition of glycoprotein to the solution. In the same manner, glycoproteins are extracted from aqueous solution by membrane formation. This is particularly useful for forensic science, purification processes, and sensors. For example, glycoproteins present in plant and animal tissue fluids such as vegetable juice, blood, or saliva can be extracted from an aqueous solution through membrane formation with organic solvents or oils floating on the surface. Membranes and large vesicles can be lifted from the surface of an aqueous medium, washed and introduced into a second solution. Microscopic micelles can be recovered by mechanical techniques such as centrifugation, filtration, evaporation, etc.

Proteins and glycoproteins are retrieved from aqueous solution by association with a lipid or a hydrocarbon. Membranes or large vesicles are lifted from the surface of the solution.

While the structure of lipo-glycoprotein membrane is not known positively, it is postulated that a sheet of hydrogen-bonded protein and sulfur-bonded chains may lie between water and lipid layers. Groups containing oligosaccharides would face the water, while nonpolar groups would be immersed in the lipid layer. The formation and preservation of stable micelles appears to depend on the association of glycoprotein with both oil and water.

The characteristic affiliation of molds and bacteria for the oil or aqueous phase of a membrane preparation provides a means of distinguishing them and separating them. Juices from most fruits support water molds that grow in the aqueous phase. However, the mold typically found in grapefruit projects hyphae into the hydrophobic phase, and will even grow in the presence of heptane. Molds found in nuts tend to form a mat of hyphae in the membrane and project a second set upward into the hydrophobic phase. Bacteria often proliferate at the aqueous surface of a lipo-glycoprotein membrane. Occasionally, a species of microbe can be found growing in the oil fraction. Thus, one can use a lipo-glycoprotein preparation as a culture medium, and then extract metabolites or the mold or bacteria per se from the aqueous or hydrophobic phase.

A large shallow dish is useful for exposing the maximum amount of glycoproteins in solution to the surface, and requires the use of more lipid to form a membrane that covers the entire surface. It is possible to effectively distribute a thin layer of lipid or hydrocarbon using an atomizer to spray it over the surface. In most of the experiments described herein, the container has an inner diameter of about 2.5 inches. About 5 ml lipid is generally used to cover the surface of the aqueous solution containing glycoproteins.

The Glycoprotein Component

The term "glycoprotein", as used herein, includes compounds known as mucoproteins and proteoglycans. The classification of glycoproteins has become complicated by recent elucidation of their structures. For example, glycosaminoglycans, once thought to be attached only in O linkages to serine and threonine side chains, have been detected in N-linkage to asparagine side chains of cells surface glycoproteins (Oxford Glycosystemns, 1994).

The properties of lipo-glycoprotein membranes vary greatly, depending on the nature and condition of component constituents and on methods used in their preparation. Many glycoproteins are fragile and become denatured or altered when exposed to a variety of chemical and physical conditions. For example, some glycoproteins are irreversibly altered by slight changes in salinity or pH. Therefore, certain commonly used laboratory methods and materials must be avoided.

It has been demonstrated that the presence of hydrated oligosaccharide moieties prevents self-aggregation of certain glycoproteins (Scott and Dodd, 1990). This may explain observed changes in solubility of some glycoproteins when they are dehydrated, frozen, or exposed to hydrophobic liquids. In general, the glycoproteins mentioned in the examples of this disclosure were obtained from fresh plant and animal tissue fluids. However, glycoproteins having similar properties can be obtained from any convenient source.

Because of its availability, ease of preparation, and known glycoprotein content, the liquid portion of fresh, unfertilized hen egg white (about 5 ml fluid per 35 ml egg white) has been used most often to study the formation and properties of lipo-glycoprotein membranes. Tissue fluids from many other animal and plant sources have also been used to produce membranes and micelles. These includes extracts from chicken skin and muscle, human saliva, bronchial secretions, blood, juices squeezed from oranges, limes, melons, grapes, plums, apples and onions. However, juices from members of the genus Solanum (nightshade), which includes vegetables such as peppers and tomatoes, have not produced lipo-glycoprotein membranes. Synthetic glycoproteins can also be used, as well as glycoproteins produced by genetically engineered plants or animals.

Once formed, lipo-glycoprotein membranes are often quite resistant to destruction. It is interesting to note that micelles formed from olive oil and the water-miscible portion of egg white are not broken by liquid detergent.

The Hydrophobic Component

Lipids float on the surface of water for two reasons. Because they are non-polar, lipids are insoluble in water, and do not, alone form stable emulsions. Secondly, lipids have lower specific gravity than water. Double bonds in the hydrocarbon chains of unsaturated oils produce kinks that prevent crystallization. For this reason, lipids containing unsaturated fatty acids are liquid at room temperature.

Olive, corn, peanut, canola, soybean, and safflower oils have been used to produce stable lipo-glycoprotein membranes and micelles. Olive oil generally produces a more flexible, less stable membrane than one made with corn, soybean, peanut, or safflower oils. Lanolin, a wax, has also been found to produce a membrane when layered on a solution containing glycoprotein. However, micelles formed from lanolin and the liquid portion of egg white may not be stored at room temperature for long periods of time.

Liquid hydrocarbons, such as hexane and heptane, have also been found to induce the production of relatively stable glycoprotein micelles. Large vesicles produced from certain glycoproteins, such as those present in liquid egg white can be lifted from solution onto a filter or a support. This property makes the vesicles and micelles attractive for retrieving components from an aqueous solution.

The membranes of the present invention can be used to detect the presence of an antigen in an aqueous solution. Recently, transgenic plants have been used to produce mammalian antibodies, which can be incorporated into membranes.

Some water miscible chemicals prevent formation of membranes by denaturing certain glycoproteins that are otherwise stable. This effect can be used to indicate the presence of pollutants in bodies of water or in manufacturing processes.

Eukaryotic plants and animals secrete glycoproteins that will bind with oil floating on the surface of water. This phenomenon can be used to collect and concentrate the glycoproteins for analysis. The oligosaccharide moieties of glycoproteins are often species specific and can also be tissue-specific.

EXAMPLES

Lifting Membrane from Solution

Peanut oil and turmeric were mixed and allowed to rest overnight. A few drops of bright yellow-stained oil were decanted and sprinkled on top of a pink solution containing 5 ml liquid egg white, 30 ml distilled water, and water-soluble McCormick food coloring. A toothpick was used to drag the oil droplets into a pattern. White filter paper was then carefully pressed onto the entire surface of the fluid. The paper was removed and examined. The area that had contacted the aqueous solution was pink. Where the paper had contacted oil, distinct orange swirls reproduced the pattern produced by the toothpick. A drop of turmeric-stained yellow oil was then placed on a corner of the paper that had not contacted any colored fluid. The paper was then washed in liquid detergent and examined again. The pink color had disappeared. An indistinct, pale yellow dot remained in the corner. However, where a membrane had been present, orange swirls remained distinct and had not bled nor washed out.

Recovery of Glycoprotein from Aqueous Medium 0.10 ml (one drop) of liquid egg white was dropped into 375 ml distilled water. The mixture was poured into a shallow glass dish measuring 7×11×2 inches. The aqueous solution, which was about ¼" deep, was covered with a thin layer of heptane sprayed from an atomizer. The dish was rocked gently for about 5 minutes. Heptane-filled vesicles of varied shapes began to form beneath the surface after about a minute. The mixture was transferred to a glass cylinder. Vesicles were collected from the surface in a large-mouthed pipette and placed on slides for microscopic examination. Clear, delicate bubbles of heptane ranged in size from 600 microns to 10 microns in diameter. When the heat of the microscope lamp caused a bubble to pop, its persistent wrinkled membrane could be seen shrinking as the heptane evaporated. Long folds indicated that a continuous, transparent membrane lay just above the micelles. When the aqueous solution and heptane had evaporated, roughly circular patches of whitish material were arranged in regular, concentric arrays spaced about 2.5 microns apart. The aqueous solution from which micelles were removed was placed back into the rectangular dish and sprayed with heptane. No micelles formed when the solution was rocked, indicating that all glycoprotein had been extracted by the initial operation.

Complete Recovery from Water of Egg White Bound in Floating Micelles

The liquid portion of five 3 month-old unfertilized hen eggs was poured into a 100 ml graduated burette containing about 80 ml of distilled water. Immediately a denser yellowish component fell to the bottom of the cylinder and began to precipitate at the interface with the water above. That fraction was allowed to escape from the stopcock. The mixture was allowed to stand for 2 hours. The lower 10 ml was allowed to escape into a shallow dish. When cold pressed olive oil was dripped onto the surface and shaken, the solution showed no tendency to form micelles. Each subsequent 10 ml aliquot was mixed separately with oil. With the exception of aliquots 4 and 5, there was a progressive increase in the tendency to form stable micelles from the bottom to the top of the solution, with the last three forming micelles immediately. More oil was dripped into each dish and mixed with a wire whisk until there was no more tendency to form micelles. Then each dish was heated in boiling water for about 4 minutes until the solution began to bubble. In every case, the water beneath the micelles was clear, indicating that all glycoprotein had been extracted by the formation of micelles. By contrast, a solution containing egg white dissolved in distilled water turned milk white when brought to a boil. Micelles from batch #7 were examined microscopically. Some contained opaque particles and bubbles in the oil fraction. However, most were clear. Very small micelles were suspended in the solution. This experiment was repeated with fresh fertilized and unfertilized eggs. By adding water to the solution before adding oil, it was possible to avoid causing the formation of an water-in-oil emulsion during the preparation of micelles.

Recovery of Oligosaccharides From Solution of Egg White and Distilled Water 30 ml steam distilled water is added to 5 ml liquid egg white in a plastic cup. Denatured proteins that settle to the bottom of the container are removed through a pipette along with about 10 ml of the aqueous solution. 5 ml corn oil is layered onto the solution and a membrane is allowed to form. Solution suspending micelles are replaced with distilled water. An N-glycosidase is introduced into the solution to cleave oligosaccharides from micelles. The solution of oligosaccharides is separated mechanically from micelles, and carbohydrates are recovered through evaporation.

The foregoing description of the specific embodiments will so fully reveal the general nature of the invention that others can, by applying current knowledge, readily modify and/or adapt for various applications such specific embodiments without departing from the generic concept, and, therefore, such adaptions and modifications should and are intended to be comprehended within the meaning and range of equivalents of the disclosed embodiments. It is to be understood that the phraseology or terminology employed herein is for the purpose of description and not of limitation.

What is claimed is:

1. A method for extracting carbohydrates from a polar solution containing at least one glycoprotein comprising:
   (a) layering at least one non-polar liquid on a polar solution containing at least one glycoprotein;
   (b) allowing a glycoprotein membrane to form at the interface between said polar solution and said non-polar liquid;
   (c) replacing the polar solution described in step (a) with water;
   (d) treating the water from step (c) with n-glycosidase to remove carbohydrate moieties from said glycoprotein;
   (d) separating the water containing the carbohydrate moieties from the protein and non-polar liquid.

2. The method of claim 1, wherein said at least one non-polar liquid is an oil.

3. The method of claim 2, wherein said oil is selected from the group consisting of olive oil, corn oil, peanut oil, canola oil, soybean oil, peppermint oil and safflower oil.

4. The method of claim 1, wherein said at least one non-polar liquid is a hydrocarbon solvent selected from the group consisting of heptane and hexane.

5. The method of claim 1, wherein said polar solution is selected from the group consisting of water, human saliva, a bronchial secretion, blood, an aqueous extract of a bodily tissue, and juice from a fruit or vegetable.

6. The method of claim 5, wherein said polar solution is human saliva.

7. The method of claim 5, wherein said polar solution is a bronchial secretion.

8. The method of claim 5, wherein said polar solution is blood.

9. The method of claim 5, wherein said polar solution is an aqueous extract of a bodily tissue.

10. The method of claim 9, wherein said aqueous extract of a bodily tissue is an aqueous extract of animal skin, or an aqueous extract of animal muscle.

11. The method of claim 5, wherein said polar solution is said juice from a fruit or vegetable.

12. The method of claim 11, wherein said juice from a fruit or vegetable is selected from the group consisting of orange juice, lime juice, melon juice, grape juice, plum juice, apple juice and onion juice.

13. The method of claim 1, further comprising agitating said non-polar and polar solution to form micelles.

14. The method of claim 13, wherein said micelles are from about 1 to 10 microns in diameter.

15. The method of claim 14, wherein said micelles are from about 1 to about 5 microns in diameter.

16. The method of claim 1, wherein said steps (c) and (d) comprise replacing said polar solution with an aqueous solution comprising a glycosidase.

* * * * *